United States Patent [19]

Johnson

[11] Patent Number: 5,347,029

[45] Date of Patent: Sep. 13, 1994

[54] DIALKYL (DIALKOXYPHOSPHINYL)METHYL PHOSPHATES AS ANTI-INFLAMMATORY AGENTS

[75] Inventor: Roy A. Johnson, Kalamazoo, Mich.

[73] Assignee: The Upjohn Company, Kalamazoo, Mich.

[21] Appl. No.: 168,441

[22] Filed: Dec. 16, 1993

Related U.S. Application Data

[63] Continuation-in-part of Ser. No. 717,428, Jun. 19, 1991, abandoned.

[51] Int. Cl.⁵ ............................................. C07C 261/00
[52] U.S. Cl. ................................ 558/158; 558/155; 558/77; 558/86; 548/112; 546/22
[58] Field of Search .................... 558/158, 155, 77, 86; 548/44, 22, 112

[56] References Cited

U.S. PATENT DOCUMENTS

| | | | |
|---|---|---|---|
| 3,808,237 | 2/2976 | Kerst | 558/90 |
| 4,309,364 | 1/1982 | Bentren et al. | 558/158 |
| 4,746,654 | 5/1988 | Breliere et al. | 514/108 |
| 4,894,469 | 1/1990 | Staendeke et al. | 558/90 |
| 4,927,814 | 5/1990 | Gall et al. | 558/158 |
| 4,942,157 | 7/1990 | Gall et al. | 514/108 |
| 5,041,428 | 8/1991 | Esomnia et al. | 558/158 |
| 5,153,183 | 10/1992 | Kawabe et al. | 558/155 |
| 5,190,930 | 3/1993 | Jaeggi | 514/89 |
| 5,254,544 | 10/1993 | Biller et al. | 558/155 |
| 5,280,022 | 1/1994 | Sohda et al. | 558/158 |

FOREIGN PATENT DOCUMENTS

207285 of 0000 United Kingdom.

OTHER PUBLICATIONS

Tromelin et al, "α Cétophosphonates et Esters Cycliques D'Hydroxymethylenes Diphosphonates Synthesis, Structures et Hydrolyse". *Phosphorous and Sulfur*, vol. 27 pp. 301–312, 1986. (See Applicants IDS).

Primary Examiner—José G. Dees
Assistant Examiner—Keith MacMillan
Attorney, Agent, or Firm—Donald L. Corneglio; Gregory W. Steele; 10

[57] ABSTRACT

Provided are novel dialkyl (dialkoxyphosphinyl)methyl phosphates of formula

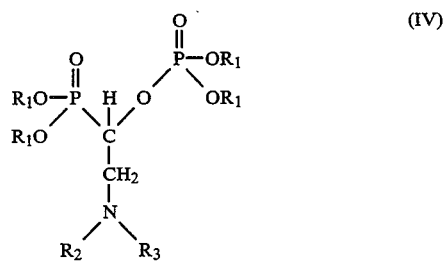

(IV)

which am useful as anti-inflammatory and anti-arthritic agents. The compounds are synthesized from the reaction of tetraethyl oxiranylidenebisphosphonate and unsubstituted or alkyl-amines. Representative compounds include 2-(benzylamino)-1-(diethoxyphosphinyl)ethyl phosphonic acid diethyl ester, 1-(diethoxyphosphinyl)-2-[2'-(1', 2', 3', 4'-tetrahydro)napthylamino]ethyl phosphonic acid diethyl ester, 2-(3-fluorobenzylamino)-1-(diethoxyphosphinyl)ethyl phosphonic acid diethyl ester, and 5,5-dimethyl-2-[2-(3-fluorobenzyl)amino-1-[(5,5-dimethyl-1,3,2-dioxaphosphorinan-2-yl)oxy]ethyl]-1,3,2-dioxaphosphorinane P,2-dioxide.

15 Claims, No Drawings

DIALKYL (DIALKOXYPHOSPHINYL)METHYL PHOSPHATES AS ANTI-INFLAMMATORY AGENTS

CROSS-REFERENCE TO RELATED APPLICATIONS

This application is a continuation of International Patent Application No. PCT/US92/04013, filed 21 May 1993; which is a continuation-in-part of U.S. Ser. No. 07/717,428, filed 19 June 1991, abandoned.

FIELD OF THE INVENTION

The invention provides novel phosphonate-phosphates, and acids and salts thereof, which are useful as anti-inflammatory and anti-arthritic agents. The invention also provides a novel process for the production of the compounds of the invention.

BACKGROUND OF THE INVENTION

There are various phosphonale-phosphates known in the art. Among these are the gem-phosphonate-phosphates, structurally characterized by having one phosphonate group ($-PO_3R_2$) and one phosphate group ($-OPO_3R_2$) bound to the same carbon atom.

The synthesis of known phosphonate-phosphates has been characterized. D. Brittelli, J. Org. Chem., 1985, 50:1845–47, reports the formation of phosphinylethenyl phosphate from chloracetyl chloride and trialkyl phosphites in ether. S. J. Fitch and K. Moedritzer, J. Amer. Chem. Sec., 1962, 84:1876–79, report the formation of 1-hydroxy phosphonate-phosphates via a base mediated isomeric rearrangement of the corresponding 1-hydroxy bisphosphonates. See also A. Tromelin, et al., Phosphorous and Sulfur, 1986, 27:301–12. None of these references disclose a utility for the compounds synthesized.

U.S. Pat. No. 4,894,469 discloses a process for making halogenated phosphonate-phosphates by reacting, first, alkylene oxide and phosphorus (III) chloride, and second, reacting the resulting phosphate trialkylesters with a halogen-acyl halide. The product is said to be useful as a fire retardant. L. M. Nguyen, et al., J. Med. Chem., 1987, 30:1426–33, report the synthesis of gem-phosphonate phosphates having activities which alter lipid metabolism and plasma high density lipoprotein cholesterol levels in rats. See also UK Patent 2,079,285. These compounds are synthesized via the reaction of dialkyl acyl phosphonates with alkyl phosphite in the presence of 80–100 reel % dialkylamine.

Other bis-phosphorus compounds, particularly the bisphosphonates, reportedly have anti-inflammatory activity, see e.g., U.S. Pat. No. 4,746,654, Australian Patent 8551-534-A (Derwent 86-212293/33), or utilities in the treatment of abnormal calcium metabolism/deposition, see e.g., U.S. Pat. No. 3,683,080, and DE 3,719,513 (Derwent 89-000580/01). However, no anti-inflammatory properties have been reported for the gem-phosphonate-phosphates.

The general mode of synthesis of the phosphonate-phosphates has been well documented. The typical procedure utilizes a reaction where the corresponding bisphosphonate undergoes rearrangement in lhe presence of excess base to titan the phosphonate-phosphate. See e.g. Nguyen, et al, J. Med. Chem., 1987, 30:1426–1433. U.S. Pat. No. 3,808,237, however, describes a scheme in which a substituted ethane polyphosphonate is reacted with an epoxidizing agent to produce the corresponding epoxy ethane diphosphonate. The epoxy ring thus formed is opened ("de-oxiranized") to form the ethane diphosphonate. The same or similar procedure is employed in the production of the various diphosphonates described in U.S. Pat. Nos. 3,940,436, 3,944,599, 3,957,858, and 3,962,318.

The compounds of the invention differ from the prior art compounds in having an amino group at position 2 of the methylene moiety. The compounds of the invention are prepared by a novel process which comprises reacting an epoxy ethane diphosphonate with an amino compound. The synthesis of the epoxy ethane diphosphonate is known and is described in U.S. Pat. No. 3,808,237.

The opening of epoxides by amines to form aminoalcohols is precedented in the literature, see for example, R. C. Larock, Comprehensive Organic Transformations, 1989, VCH Publishers, pp. 508–511. However, the opening of the epoxide tetramethyl oxiranylidenebisphosphonate by amines, followed by rearrangement to produce the compounds of the invention, has not been reported.

Known gem-phosphonate-phosphates reportedly display lipid-lowering and antiatherosclerotic activity. However, no anti-inflammatory properties have been reported for gem-phosphonate-phosphates.

This invention discloses novel gem-phosphonate phosphates useful as antiinflammatories and in the treatment of arthritis. This invention also provides a process for the synthesis of the compounds of the invention.

U.S. Pat. No. 4,746,654 discloses bisphosphonates useful as anti-inflammatory agents. The compounds disclosed, however, are not related to the compounds of lhe invention.

Australian Patent 8551-534-A (Derwent 86-212293/33) discloses bisphosphonic acids and derivatives useful in treating abnonnal calcium and phosphorous metabolism and are useful in treating arthritis. The compounds disclosed, however, are not structurally related to the compounds of the invention.

UK Patent 2 079 285 discloses bisphosphonic acids and phosphonic-phosphates, and derivatives thereof, useful as hypolipemic agents. The structures disclosed neither encompass the compounds of the invention nor does the patent disclose an anti-inflammatory utility.

A published European patent application, EP 320 455, discloses bisphosphonic acids derivatives useful as regulators of calcium metabolism and as anti-inflammatories. The compounds disclosed, however, are not related to the compounds of the invention.

A published European patent application, EP 252 504, discloses bisphosphonic acids and derivatives thereof useful as regulators of calcium metabolism. The compounds disclosed, however, are not related to the compounds of the invention.

L. M. Nguyen, et al, J. Med. Chem., 1987, 30: 1426–33, report gem-phosphonate-phosphates which have anti-atherosclerotic potential. The compounds lack the amino group of the present invention.

U.S. Pat. No. 4,894,469 discloses a process for making halogenated phosphonophosphoric acid and esters thereof useful as fire retardants. The compounds disclosed lack the amino group of the present invention.

U.S. Pat. No. 3,808,237 discloses the synthesis of substituted epoxy ethane polyphosphates (bisphosphonates), which are useful as a starting material for the compounds of the invention. The compounds are disclosed as having utility as fire retardants.

S. J. Fitch and K. Moedritzer, J. Amer. Chem. Soc., 1962, 84:1876–79, report the formation of 1-hydroxy phosphonate-phosphates. However, the compounds lack the amino group of the present invention.

D. Brittelli, J. Org. Chem., 1985, 50:1845–47, describes the synthesis of phosphonate-phosphates from chloroacetyl chloride. However, the compounds lack the amino group of the present invention.

A. Tromelin, et al, Phosphorous and Sulfur, 1986, 27:301–12, report isomerization and hydrolysis studies on hydroxy methylene diphosphonates. The resulting compounds, however, lack the amino group of the present invention.

M. Kanaan and R. Burgada, Phosphorous and Sulfur, 1988, 37:217–29, disclose the synthesis of phosphonate-phosphates via the rearrangement reaction of bisphosphonates.

SUMMARY OF THE INVENTION

This invention provides a compound of formula IV (Chart A) wherein $R_1$ is independent and selected from the group consisting of hydrogen, $C_1$–$C_{10}$ alkyl, and —$C_6H_5$;

adjacent $R_1$ taken together may be —$CH_2(CH_2)_nCH_2$— or —$CH_2C(CH_3)_2CH_2$—;

$R_2$ is selected from the group consisting of hydrogen, $C_1$–$C_{10}$ alkyl, $C_3$–$C_7$ cycloalkyl, —$CH_2CH=CH_2$, —$CH_2CH_2OH$, —$CH_2(CH_2)_nAr$, —$CH_2CH_2OCH_2Ar$, —$CH(C_6H_5)_2$, and 1'- or 2'-(1',2',3',4'-tetrahydro)naphthylene;

$R_3$ is selected from the group consisting of hydrogen, $C_1$–$C_{10}$ alkyl, —$CO(CH_2)_mCH_3$, —$CO_2CH_2Ar$, and —COAr;

n is 0, 1, or 2;

m is 0 thru 9;

Ar is selected from the group consisting of
(a) phenyl, 1- or 2-naphthyl, 3-indolyl, 2-, 3-, or 4-pyridinyl, or 1-imidazolyl,
(b) phenyl optionally substituted with 1 thru 5 —F or —Cl,
(c) phenyl optionally substituted with 1 thru 3 —Br, —I, —$CF_3$, —$R_4$, or —$OR_4$,
(d) phenyl substituted with —$COOR_4$, —$OCOR_4$, —$SO_2NH_2$, —$NHSO_2R_4$, and —$NHCOR4$;

$R_4$ is $C_1$–$C_5$ alkyl; provided, however, when $R_1$ is —$C_2H_5$, neither $R_2$ nor $R_3$ may be —$C_3H_7$ and pharmaceutically acceptable salts thereof.

This invention also provides a process For making a compound of formula IV in which $R_1$ is independent and selected from the group consisting of $C_1$–$C_{10}$ alkyl and —$C_6H_5$;

adjacent $R_1$ taken together may be —$CH_2(CH_2)_nCH_2$— or —$CH_2C(CH_3)_2CH_2$—;

$R_2$ is selected from the group consisting of hydrogen, $C_1$–$C_{10}$ alkyl, $C_3$–$C_7$ cycloalkyl, —$CH_2CH=CH_2$, —$CH_2CH_2OH$, —$CH_2(CH_2)_nAr$, —$CH_2CH_2OCH_2Ar$, —$CH(C_6H_5)_2$, and 1'- or 2'-(1',2',3',4'-tetrahydro)naphthylene;

$R_3$ is selected from the group consisting of hydrogen, $C_1$–$C_{10}$ alkyl, —$CO(CH_2)_mCH_3$, —$CO_2CH_2Ar$, and —COAr;

n is 0, 1, or 2;

m is 0 thru 9;

Ar is selected from the group consisting of
(a) phenyl, 1- or 2-naphthyl, 3-indolyl, 2-, 3-, or 4-pyridinyl, or 1-imidazolyl,
(b) phenyl optionally substituted with 1 thru 5 —F or —Cl,
(c) phenyl optionally substituted with 1 thru 3 —Br, —I, —$CF_3$, —$R_4$, or —$OR_4$,
(d) phenyl substituted with —$COOR_4$, —$OCOR_4$, —$SO_2NH_2$, —$NHSO_2R_4$, and —$NHCOR4$;

$R_4$ is $C_1$–$C_5$ alkyl; provided, however, when $R_1$ is —$C_2H_5$, neither $R_2$ nor $R_3$ may be —$C_3H_7$ comprising the steps of:
(a) reacting an epoxy ethane bisphosphonate compound of formula III with an amine at a temperature and for a period of time to form reaction products comprising substantially compound of formula IV;
(b) extracting the reaction products;
(c) purifying the product via a chromatography procedure.

DETAILED DESCRIPTION OF THE INVENTION

The compounds of the invention are synthesized following techniques known by those skilled in the art of organophosphorous chemistry. For a general review see R. Engel, 1988, Synthesis of Carbon-Phosphorous Bonds, CRC Press, or alternatively, the required techniques may be readily acquired by reference to standard laboratory manuals, for example, B. S. Furniss, et al, 1989, Vogel's Textbook of Practical Organic Chemistry, 5th Ed., Longman Scientific and Tectchnical (publisher), all of which are incorporated by reference.

The synthesis of the compounds of formula IV is briefly described here and in more detail below. Referring to Chart A, paraformaldehyde in dialkyamine-methanol (formula Ia) is reacted with a methylene diphosphonate (formula Ib) to produce an ethylidene-1,1-phosphonate (formula II); these reactants (Ia and Ib), as well as suitable reaction conditions, are known by those skilled in the art. The compounds of formula II are also known, see e.g. U.S. Pat. Nos. 4,894,469 and 3,808,237. The methylene diphosphonate (Ib) is substituted, i.e. $R_1$ is other than hydrogen. In addition, methylene (diethyl)diphosphonate is available from commercial sources. It is preferred that $R_1$ is ethyl (—$CH_2CH_3$). When adjacent $R_1$ are taken together it is preferred that it is —$CH_2C(CH_3)_2CH_2$—. It is preferred that $R_2$ is hydrogen and ihat $R_3$ is either benzyl or —$CH_2$—(3'-fluoro)benzyl.

The ethylidene-1,1-phosphonate (II) is subsequently reacted with alkaline hydrogen peroxide to produce the epoxide, oxiranylidenebisphosphonate (formula III). The epoxide is then treated with an amine to to effect ring opening and substitution (formula IV). The amine may be substituted at either, or both, positions $R_2$ and $R_3$, or the amine may be unsubstituted. The amines are known in the art and are readily available from commercial sources.

The preparation of the acid (IV), i.e. where $R_1$ is hydrogen, may be achieved by exposure of the corresponding methyl or ethyl ester (IV) to trialkyl silyl halides ($R_aR_bR_c$Si-X), most commonly trimethyl silyl halide, followed by hydrolysis of the intermediately formed silyl ester (—$SiR_aR_bR_c$). (See e.g., C. E. McKenna, et al, Tetr.Lett., 1977, 155, and R. Bittman, et al, Chem.Phys.Lipids, 1984, 34:201). Cleavage of these esters (IV) may also be achieved using cesium fluoride (CsF) or sodium iodide (NaI) following procedures known in the art.

When $R_1$ is trichloroethyl ($-CH_2CCl_3$), an alternative preparation of the acid form of IV may be accomplished by the use of a variety of reagents, for example, zinc, zinc amalgam, sodium naphthalide, cesium fluoride, and tetra-n-butyl ammonium fluoride. This procedure is known, see e.g., R. L. Letsinger and W. B. Lunsford, J.Am.Chem.Soc., 1976, 98:3655, and K. K. Ogilvie, et al, J.Am.Chem.Soc., 1977, 99:1277.

It is readily apparent that by making slight adjustments to the reaction parameters discussed here, and including the use of protecting groups when necessary, one skilled in the art may effect the mono-, di-, tri, and tetra-acid forms of IV. In addition these and other known techniques are useful in the independent selection of esters for $R_1$, e.g. a compound of formula IV wherein $R_1$ consists of two methyl esters and two ethyl esters.

Any pharmaceutically acceptable salt may be employed to convert either the acid or ester form of IV to the respective salt. The acid addition salts of IV may be prepared by reaction with an appropriate acid, e.g. hydrogen chloride, hydrobromic acid, taratic acid, succinic acid, and the like. The base addition salts of the acid form of IV are prepared by reacting the acid with an appropriate base, for example, sodium, potassium, calcium, magnesium, ethanolamine, and the like. These addition reactions are well known in the art and require no special mention.

At the completion of any of the synthetic steps, the reaction mixture may be treated by conventional chemical processing and/or purification procedures, e.g. dilution, solvent partitioning, filtration, concentration, and cooling, to separate the products from the reactants. One or more solvents, in one or more extractions have been found useful for this purpose. For example, ether, methylene chloride, and ethyl acetate are found to be useful for the separation and extraction following the ring opening and substitution by the amine. The compounds of the invention are oils or liquids and are thus readily separated by chromatographic methods known to be useful for this propose by those skilled in the art of chemical purification and analysis. (See, for example, B. S. Furniss, et al, 1989, Vogel's Textbook of Practical Organic Chemistry, 5th Ed., Longman Scientific and Technical (publisher)).

The compounds of the invention have pharmacological activity as anti-inflammatory or anti-arthritic agents. Thus, the compounds of the invention are useful in humans and animals in the treatment of diseases characterized by abnormal phosphate and/or calcium metabolism. These diseases include: osteoporosis, Paget's disease, periodontal disease, rheumatoid arthritis, osteoarthritis, chondrocalcinosis, septic arthritis, neuritis, bursitis, soft tissue mineralization disorders, ankylosing spondylitis, atherosclerosis, multiple myeloma of bone, metastatic bone disease, chronic granulomatous diseases and mitral valve calcification. The compounds of the invention are also useful for treatment of inflammation in humans and animals.

The dialkyl (dialkoxyphosphinyl)methyl phosphates of the invention (IV) can be administered orally, parenterally (intramuscularly, intravenously, subcutaneous or intraperitoneally), transdermally or intra-articularly or by suppository. The dose is about 0.01 gm/patient/day to about 1.0 gm/patient/day.

The gem-phosphonate-phosphates (IV) can be used alone or in combination with offset pharmaceuticals as is known to those skilled in the art. The exact route of administration, dose, frequency of administration, of a particular gem-phosphonate-phosphate (IV), depends on the particular disease or condition, the severity of the disease or condition, the age, general physical condition, weight, other clinical abnormalities etc. of the particular patient to be treated as is known to those skilled in the art.

To achieve maximum efficacy in the treatment of the diseases outlined above, intermittent as well as continual daily therapy may be indicated, as is known to those skilled in the art. See, for example, "Long-Term Effects of Dichloromethylene Diphosphonate in Paget's Disease of Bone", P. D. Dumas, et al., J. Clin. Endocrinol. Metab., 54, 837 (1982); "Paget's Disease of Bone Treated in Five Days With AHPrBP(APD) Per Os", D. Thiebaud, et al., J. Bone. Min. Res., 2, 45 (1987); "A Single Infusion of the Bisphosphonate AHPrBP(APD) as Treatment of Paget's Disease of Bone" D. Thiebaud, et al., The Am. J. Med., 85, 207 (1988); "A Double Blind Placebo-controlled Trial of Diphosphonate (APD) Therapy in Rheumatoid Arthritis - Preliminary Results", S. H. Ralston, et al., Calcif. Int., 42, A23 (1988); "Treatment of Hypercalcemia of Malignancy With Intermittent Single Infusions of 3-Amino-1-hydroxypropylidene-1,1-bisphosphonate (APD)", D. Rischin, et al., Aust. NZ. J. Med., 18, 736 (1988); "Reduced Morbidity From Skeletal Metastases in Breast Cancer Patients During Long-Term Bisphosphonate (APD) Treatment" A. Th. van Holten-Verzantvoort, et al., The Lancet (10-31-87), p. 983; "Sclerosis of Lyric Bone Metastases After Disodium Aminohydroxypropylidene Bisphosphonate (APD) in Patients with Breast Carcinoma" A. R. Morton, et al., British Med. J., 297, 772 (1988); "Two Year Follow-up of Bisphosphonate (APD) Treatment in Steroid Osteoporosis" I. R. Reid, et al., The Lancet (11-12-88), p. 1144.

Definitions

The definitions which follow are for terms used throughout the specification and claims. All temperatures are in degrees Centigrade. TLC refers to thin-layer chromatography. p-TSA refers to p-toluenesulfonic acid monohydrate. TEA refers to triethylamine. Brine refers to an aqueous saturated sodium chloride solution. IR refers to infrared spectroscopy. CMR refers to $^{13}C$ magnetic resonance spectroscopy; chemical shifts are reported in ppm ($\delta$) downfield from tetramethylsilane. NMR refers to nuclear magnetic resonance spectroscopy; chemical shifts are reported in ppm ($\delta$) downfield from tetramethylsilane. $\phi$ refers to phenyl ($C_6H_5$). MS refers to mass spectrometry expressed as m/e or mass/charge unit. $[M+H]^+$ refers to the positive ion of a parent plus a hydrogen atom. EI refers to electron impact. CI refers to chemical ionization. FAB refers to fast atom bombardment. Alkyl includes both linear and branched carbon-carbon chains. Ether refers to diethyl ether. Pharmaceutically acceptable refers to those properties and/or substances which are acceptable to the patient from a pharmacological/toxicological basis and to the manufacturing pharmaceutical chemist from a physical/chemical basis regarding composition, formulation, stability, patient acceptance, and bioavailability.

When solvent pairs are used, the ratios of solvents used are volume/volume (v/v).

Preparation 1 Tetraethyl ethylidene- 1,1 -diphosphate (II)

Paraformaldehyde (104.2 g) and diethylamine (50.8 g) are combined in methanol (2 L), warmed until clear, then treated with methylene bisphosphonic acid, tetraethyl ester (190.09 g) and refluxed for 18 hours. The sample is then concentrated, methanol added, the methanol removed by heat and reduced pressure, and toluene is added and removed by heat and reduced pressure. The residue is dissolved in toluene (1:1), treated with p-TSA (0.5 g) and refluxed through a Dean Stark trap for 18 hours. The sample is concentrated under reduced pressure with heat, dissolved in methylene chloride, washed twice with water, dried with magnesium sulfate, and concentrated under reduced pressure with heat. The sample is purified by distillation at reduced pressure to give the title compound (bp=140° ); MS (m/e) 300, 285, 273, 255, 245, 227, 217, 199, 192, 181, 163, 153 and 135; IR (neat) 2984, 2934, 2909, 1651, 1580, 1479, 1444, 1392, 1254, 1166, 1098, 1042, 1025, 974, 855, 813 and 800 cm-1; NMR (CDCl3) 7.1, 6.7, 4.1 and 1.3 δ.

This compound is known, see published European Patent Application EP 221 611.

Preparation 2 Tetraethyl oxiranylidenebisphosphonate (III)

A solution of tetraethyl ethylidene-1,1-diphosphonate (Preparation 1, 1.510 g, 0.0050 mol) in 95% ethanol (5 ml) is treated with 30% aqueous hydrogen peroxide (1 ml) and sodium bicarbonate (0.424 g). The resulting mixture is stirred at room temperature for two hours, diluted with brine and extracted with methylene chloride (2x). The combined organic extracts are dried over magnesium sulfate, filtered, and concentrated under reduced pressure to give tetraethyl oxiranylidenebisphosphonate tetraethyl oxiranylidenebisphosphonate as a clear, colorless oil (1.472 g, 0.00465 mol). No further purification of the product is performed. IR (neat): 1260, 1026, 1023, and 978 cm-1; 1H NMR (CDCl3TMS) δ 4.28–4.19, 3.28, 1.37; $^{13}$C NMR (CDCl3) δ 63.44, 49.36, 47.24, 16.17; $^{31}$P NMR (CDCl3) δ 13.85; Mass spectrum: 316.0840 m/e, $C_{10}H_{22}O_7P_2$ requires 316.0841.

Preparation 3 2,2'-(1,1-Oxiranyl)bis[5,5-dimethyl-1,3,2-dioxaphosphorinane] 2,2'-dioxide (III)

1,3,2-dioxaphosphorinane, 2,2'-ethylidene bis(5,5'-dimethyl)-2,2'-dioxide is prepared following the procedure described in International Application PCT/US91/05554 (publication WO92/03451). A solution of 1,3,2-dioxaphosphorinane, 2,2'-ethylidene bis(5,5'-dimethyl)-2,2'-dioxide (1.146 g, 0.0035 mole) in methylene chloride (7 mL) is cooled to 0°-5° by means of an ice-water bath. This solution is treated with hydrogen peroxide (0.7 mL, 30% solution) in a single lot, followed by solid sodium bicarbonate (0.40 g, 0.0048 mole). The mixture is allowed to stir overnight at room temperature. The mixture is diluted with methylene chloride and water and the layers separated. The aqueous layer is extracted with methylene chloride(2x). The combined layers are dried (MgSO4), filtered and concentrated in vacuo to obtain 1.024 g (86% yield) of the title compound as a white solid. A portion of the crude material is crystallized from ethyl acetate to obtain colorless crystals: mp 143.3–144.3° dec. 1H NMR (CDCl3/TMS) δ 4.58 (d, J=10.9 Hz, 2H, CH2OP(O)), 4.43 (d, J=10.6 Hz, 2H, CH2OP(O)), 4.06–3.97 (m,4H, CH2OP(O)), 3.34 (t, J=5.5 Hz, 2H, CH2), 1.31 (s, 3H, CH3), 0.94 (s, 3H, CH3); $^{13}$C NMR (CDCl3) δ 78.82 (d, J=107.9 Hz, CH2OP(O)), 49.25 (t, J=175.2 Hz, P(O)C-P(O)), 48.52 (CH2CP(O)), 32.60 (C(CH3)2), 22.09, 20.54; $^{31}$P NMR (CDCl3) δ 4.426.

Anal. Calcd. for $C_{12}H_{22}O_7P_2$: C, 42.36; H, 6.52. Found: C, 42.41; H, 6.66.

EXAMPLE 1

2-(Cyclohexylamino)-1-(diethoxyphosphinyl)ethyl phosphoric acid diethyl ester A solution of cyclohexylamine (3.6 ml, 3.14 g, 0.0316 mol) in ether (3 ml) is mixed with tetraethyl oxiranylidenebisphosphonate (Preparation 2, 2.066 g, 0.00632 mol) and stirred at room temperature for 24 hours. Additional cyclohexylamine (2.601 g, 0.026 mol) is added and stirring continued until TLC (25% acetonitrile in ethyl acetate, 50% acetone in methylene chloride) reveals that most of the starting epoxide is consumed. The reaction mixture is diluted with ether (60 ml) and brine (60 ml) is added. The layers are separated and the aqueous layer is extracted with ether (3×60 ml), methylene chloride, and ethyl acetate. The combined extracts are dried (magnesium sulfate), filtered, and concentrated to give 3.233 g of crude product. Flash chromatography (400 g silica gel) of the crude product is casted out eluting with increasing proportions (from 0 to 10%) of 10% ammonium hydroxide/methanol in acetonitrile. The reactions containing the desired product are combined to give 1.046 g (0.00251 mol, 40%) of 2-(cyclohexylamino)-1-(diethoxyphosphiny)ethyl phosphoric acid diethyl ester as a colorless oil; 1H NMR (CDCl3, TMS) δ 4.80–4.70, 4.26–4.13, 3.21–3.00, 2.52–2.45, 1.89–1.59, 1.38–1.02; $^{13}$C NMR (CDCl3) δ72.46, 64.19, 62.80, 55.67, 46.57, 33.14, 32.73, 25.86, 24.66, 24.59, 1631–1584; $^{31}$P NMR (CDCl3) δ 17.61, -1.89; Mass spectrum 416.1968, $C_{16}H_{35}NO_7P_2$ requires 416.1967. Anal. Calcd. for $C_{16}H_{35}NO_7P_2$: C, 46.26; H, 8.49; N, 3.37. Found: C, 45.96; H, 8.58; N, 3.59.

EXAMPLE 2

1-(Diethoxyphosphinyl)-2-[(2'-hydroxy)ethylamino]ethyl phosphoric acid diethyl ester A mixture of tetraethyl oxiranylidenebisphosphonate (Preparation 2, 2.106 g, 0.0066 mol) and ethanolamine (7, 4.0 ml, 4.07 g, 0.066 mol) is stirred at room temperature for 18 hours after which TLC (10% methanol in acetone) revealed that the reaction is complete. Ether (60 ml) and brine (60 ml) are added to the reaction mixture and the layers are separated. The aqueous layer is extracted further with either (3×60 ml), ethyl acetate, and methylene chloride. The combined organic extracts are dried (magnesium sulfate), filtered, and concentrated to give 1.173 g of crude product. This material is purified by flash chromatography (192 g silica gel, 45 ml fractions) using 5% of 10% NH4OH/CH3OH in methylene chloride for elution. Fractions 33–58 contained the desired product and are pooled to yield 0.665 g (0.00176 mol, 26%) of 1-(diethoxyphosphinyl)-2-[(2'-hydroxy)ethylamino]ethyl phosphoric acid diethyl ester as a colorless oil; 1H NRM (CDCl3, TMS) δ 4.78–4.70, 4.26–4.12, 3.63, 3.15, 3.13, 2.93–2.86, 2.81–2.74, 1.38–1.33; $^{13}$C NMR (CDCl3) δ 72.02, 64.28, 62.96, 60.45, 50.40, 49.12, 16.27–15.67; $^{31}$P NMR (CDCl3) δ 17.58,-1.87; Mass specimen 378.1445, $C_2H_{29}NO_8P_2$ requires 378.1447.

EXAMPLE 3

2-(Benzylamino)-1-(diethoxyphosphinyl)ethyl phosphoric acid diethyl ester

A mixture of tetraethyl oxiranylidenebisphosphonate (Preparation 2, 2.085 g, 0.00632 mol) and benzylamine (3.40 g, 0.0316 mol) in ether (4 ml) is stirred at room temperature for 18 hours, after which TLC (50% ethyl acetate in methanol, 50% acetone in hexane) indicates that some epoxide remained unreacted. Additional benzylamine (2.94 g, 0.0274 mol) is added and stirring continues another 24 hours. Volatiles are removed in vacuo and the residue is chromatographed (flash, 400 g, silica gel, 45 ml fractions) using 2.5 to 5% of 10% $NH_4OH/CH_3OH$ in methylene chloride to elute the column. The desired product eluted in fractions 94–104 which are pooled to give 10 (1.069 g, 0.00253 mol, 40%) as a colorless oil; $^1H$ NMR ($CDCl_3$, TMS) δ7.34–7.23, 4.87–4.77, 4.24–4.07, 3.88, 3.78, 3.14–3.09, 1.36–1.24; $^{13}C$ NMR ($CDCl_3$) δ 139.80, 128.36, 128.14, 126.98, 72.29, 64.26, 62.99, 53.07, 49.24, 16.49–15.99; $^{31}P$ NMR ($CDCl_3$) δ 17.55,–1.90; Mass spectrum 424.1655, $C_{17}H_{31}NO_7P_2$ requires 424.165.

EXAMPLE 4

1-(Diethoxyphosphinyl)-2-[2'-(1',2',3',4'-tetrahydro)-naphthylamino]ethyl phosphoric acid diethyl ester A mixture of tetraethyl oxiranylidenebisphosphonate (Preparation 2, 2.015 g, 00637 mol) and 1,2,3,4-tetrahydronaphth-2-ylamine (2.142 g, 0.0146 mol) is stirred at room temperature for two days. Additional 1,2,3,4-tetrahydronaphth-2-ylamine (1.017 g, 0.0032 mol) is added and the mixture stirred another eight days. The mixture is chromatographed (flash, 200 g silica gel) using 10% acetone in chloroform for elution of the column. The product, 1-(diethoxyphosphinyl)-2-[2'-(1',2',3',4'-tetrahydro)naphthylamino]ethyl phosphoric acid diethyl ester (1.262 g, 0.00272 mol, 42%) is obtained as a viscous oil; $^1H$ NMR ($CDCl_3$, TMS) δ 7.08, 4.84–4.72, 4.23–4.09, 3.32–3.10, 3.05–2.90, 2.85–2.70, 2.63–2.55, 2.10–1.95, 1.70–1.50, 1.38–1.24; $^{13}C$ NMR ($CDCl_3$) δ 135.96, 134.83, 129.08, 128.42, 125.52, 125.42, 72.48, 64.15–63.94, 62.95–62.56, 52.40, 52.31, 46.90, 46.85, 46.81, 36.43, 35.96, 29.31, 28.56, 27.50, 27.22; $^{31}P$ NMR ($CDCl_3$) δ 17.76,–2.00; Mass spectrum 464.1975 m/e, $C_{20}H_{35}NO_7P_2$ requires 464.1967.

EXAMPLE 5

2-[(3'-Fluoro)benzylamino]-1-(diethoxyphosphinyl)ethyl phosphoric acid, diethyl ester A solution of 3-fluorobenzylamine (2.171 g, 0.0173 mole) and tetraethyl oxiranylidenebisphosphonate (Preparation 2, 1.097 g, 0.0034 mole) in ether (2 mL) is stirred at room temperature for 24 hours. TLC (4% methanol in methylene chloride) reveals that the starting material (epoxide) is consumed. The solvent is removed in vacuo and the remaining residue is chromatographed twice (flash, 0.040–0.063 mm silica gel, 2% methanol in methylene chloride) to give 2-[(3'-fluoro)benzylamino]-1-(diethoxyphosphinyl)ethyl phosphoric acid diethyl ester (0.344 g, 0.00078 mole, 23%) as a colorless oil. $^1H$ NMR ($CDCl_3$/TMS) δ 7.30–7.23, 7.11–7.06, 6.96–6.89, 4.83–4.77, 4.25–4.08, 3.88, 3.78, 3.10, 1.94, 1.36–1.26; $^{13}C$ NMR ($CDCl_3$) δ 163.0, 142.5, 129.6, 123.4, 114.6, 113.6, 72.0, 64.2–64.1, 63.0–62.8, 52.3, 49.0, 18.0–15.8; $^{31}P$ NMR ($CDCl_3$) δ 17.47,–1.95; Mass Spectrum: 441.1472 ($C_7H_{30}FNO_7P_2$ requires 441.1481);

Anal. Calc. for $C_{17}H_{30}FNO_7P_2$: C, 46.26; H, 6.85; N, 3.17. Found: C, 46.22; H, 6.96; N, 3.16.

EXAMPLE 6

1-(Diethoxyphosphinyl)-2-[(3'-pyridyl)methylamino]ethyl phosphoric acid diethyl ester A solution of 3-(aminomethyl)pyridine (3.406 g, 0.03 15 mole) and tetraethyl oxiranylidenebisphosphonate (Preparation 2, 2.001 g, 0.0063 mole) in ether (6 mL) is stirred at room temperature for 24 hours. TLC (7% of a 10% $NH_3/CH_3OH$ solution in methylene chloride) indicates that some epoxide remains unreacted. The solvent is removed in vacuo and the remaining residue is chromatographed (flash, 0.040–0.063 mm silica gel, 23 cm height, 8 cm wide, 4% of a 10% $NH_3/CH_3OH$ in methylene chloride, 30 mL fractions). Fractions 104 to 132 are pooled and concentrated to give 1 -(diethoxyphosphinyl)-2-[(3 '-pyridyl)methylamino]ethyl phosphoric acid diethyl ester (1.216 g, 0.0029 mole, 45%) as a yellow oil; $^1H$ NMR ($CDCl_3/TMS$) δ 8.53, 8.46, 7.68, 7.21, 4.82–4.72, 4.21–4.04, 3.87, 3.75 3.08, 1.95, 1.36–1.22; $^{13}C$ NMR ($CDCl_3$) δ 149.39, 148.24, 135.52, 134.92, 123.07, 71.82, 64.09–63.95, 62.84–62.63, 50.08, 48.97, 16.20–15.69; $^{31}P$ NMR ($CDCl_3$) δ 17.28,−2.03; Mass Spectrum: 424.1529 ($C_{16}H_{30}N_2O_7P_2$ requires 424.1528); Anal. Calc. for $C_{16}H_{30}N_2O_7P_2$: C, 45.29; H, 7.13; N, 6.60. Found: C, 45.38; H, 7.24; N, 6.65.

EXAMPLE 7

1-(Diethoxyphosphinyl)-2-[2'-(3'-indolyl)ethylamino]ethyl phosphoric acid diethyl ester A solution of tryptamine (5.06 g, 0.0315 mole) and tetraethyl oxiranylidenebisphosphonate (Preparation 2, 2.001 g, 0.0063 mole) in methanol is stirred at room temperinure for 24 hours. TLC (7% of a 10% $NH_3/CH_3OH$ solution in methylene chloride) reveals that starting material is consumed. The solvent is removed in vacuo and the remaining residue is chromatographed (flash, 0.040–0.063 mm, silica gel, 24 cm height, 8 cm wide, 2% to 5% of a 10% $NH_3CH_3OH$ solution in methylene chloride, 40 mL fractions). Fractions 118 to 156 are pooled and concentrated to give 1-(diethoxyphosphinyl)-2-[2'-(3''-indolyl) ethylamino]ethyl phosphic acid diethyl ester (1.672 g, 0.0036 mole, 57%) as a dark yellow oil. $^1H$ NMR ($CDCl_3/TMS$) δ 8.16, 7.61, 7.36–7.34, 7.20–7.04, 4.80–4.72, 4.21–4.02, 3.16–3.11, 3.09–2.92, 1.37; $^{13}C$ NMR ($CDCl_3$) δ 136.08, 127.18, 121.73, 121.64, 118.93, 118.54, 113.49, 110.84, 72.14, 64.01–63.89, 62.81–62.58, 49.60, 49.20, 25.52, 16.23–15.73; $^{31}P$ NMR ($CDCl_3$) δ 17.75, -2.16; Anal. Calc. for $C_{20}H_{34}N_2O_7P_2$: C, 50.42; H, 7.19; N, 5.88; Found: C, 50.29; H, 7.21; N, 5.89.

EXAMPLE 8

2-[Acetyl(3'-fluoro)benzylamino]-1-(diethoxyphosphinyl)ethyl phosphoric acid diethyl ester A solution of 2-[(3'-fluoro)benzylamino]-1-(diethoxyphosphinyl)ethyl phosphoric acid, diethyl ester (Example 5, 0.120 g, 0.272 mmole) in water (0.08 mL) and acetic acid (0.081 mL) is prepared at room temperature and is cooled to 0°–5° C. by means of an ice-water bath. The solution is treated with acetic anhydride (0.03 g, 0.30 mmole) and is stirred for half an hour. The low temperature bath is removed and the mixture is stirred for an hour at room temperature. Volatiles are removed under high vacuum to obtain 2-[acetyl(3'-fluoro)benzylamino)-1-(diethoxyphosphinyl)ethyl phosphoric acid diethyl ester as a colorless oil in quantitative yield. $^1$H NMR (CDCl$_3$/TMS) δ 7.37–7.42, 7.10–6.85, 5.17, 5.06, 4.90, 4.75, 4.61, 4.26–4.09, 3.86–3.66, 3.52–3.40, 2.23, 2.11, 1.39–1.26; $^{13}$C NMR (CDCl$_3$) δ 171.88, 177.15, 163.28, 139.49, 130.61, 130.17, 123.83, 121.77, 115.06, 114.57, 114.46, 113.21, 70.57, 69.80, 64.69–63.13, 52.91, 47.36–46.72, 21.78, 16.49–16.10; $^{31}$P NMR (DMSO) δ 21.21, 20.93, -2.83, -2.63; Mass Spectrum: 483.1574 (C$_{19}$H$_{32}$FNO$_8$P$_2$ requires 483.1587).

EXAMPLE 9

1-(Diethoxyphosphinyl)-2-[3'-(1'-imidazolyl)propylamnino]ethyl phosphoric acid diethyl ester A solution of 1-(3-aminopropyl)imidazole (3.96 g, 0.0317 mole) and tetraethyl oxiranylidenebisphosphonate (Preparation 2, 2.003 g, 0.0063 mole) in ether (4 mL) and methanol (4 mL) is stirred at room temperature for 24 hours. TLC (15% of a 10% NH$_3$/CH$_3$OH solution in methylene chloride) indicates that some epoxide remains unreacted. The reaction mixture is allowed to stir for another 24 hours and is placed in the refrigerator for 72 hours. The solvent is removed in vacuo and tim remaining residue is chromatographed (flash, 0.040–0.063 mm silica gel, 28 cm height, 8 cm wide, 3% of a 10% NH$_3$/CH$_3$OH solution in methylene chloride) to give 1.167 g of a slightly impure product. A second chromatography is perforated (8% to 24% methanol in ethyl acetate and 5% of a 10% NH$_3$/CH$_3$OH solution in ethyl acetate) to give 1-(diethoxyphosphinyl)-2-[3'-(1''-imidazolyl)propylamino]ethyl phosphoric acid diethyl ester (1.001 g, 0.0023 mole, 36%) as a dark yellow oil. $^1$H NMR (CDCl$_3$/TMS) δ 7.49, 7.05, 6.93, 4.78–4.68, 4.25–4.11, 4.06, 3.07, 2.68, 2.54, 1.91, 1.77, 1.38–1.32; $^{13}$C NMR (CDCl$_3$) δ 137.30, 129.43, 118.89, 72.11, 64.36, 63.15–62.94, 49.80, 45.27, 44.35, 31.19, 16.55–16.09; $^{31}$P NMR (CDCl$_3$) δ 17.40, -1.95; Anal. Calc. for C$_{16}$H$_{33}$N$_3$O$_7$P$_2$: C, 43.54; H, 7.53; N, 9.52. Found: C, 43.23; H, 7.38; N, 9.65.

EXAMPLE 10

1-(Diethoxyphosphinyl)-2-(2'-propen-1'-ylamino)ethyl phosphoric acid diethyl ester A solution of allylamine (2.86 g, 0.05 mole) and tetraethyl oxiranylidenebisphosphonate (Preparation 2, 3.00 g, 0.0095 mnole) in methanol (20 mL) is cooled to 0°–5° C. by means of an ice-water bath. The mixture is stirred till the low temperature bath expires and then stirring is continued overnight at room temperature. TLC (10% of a 10% NH$_3$/CH$_3$OH solution in methylene chloride) indicates that starting material is consumed. The solvent and excess of allylamine are removed in vacuo to give 3.621 g of crude material from which 1.025 g is chromatographed (flash, 160 g, 0.0403–0.063 mm silica gel, 4 cm wide, 20% to 30% acetone in methylene chloride) to give 1-(diethoxyphosphinyl)-2-(2'-propen-1'-ylamino)ethyl phosphoric acid diethyl ester (0.635 g, 63% overall yield) as a clear oil. $^1$H NMR (CDCl$_3$) δ 5.87, 5.19, 5.09, 4.83–4.72, 4.26–4.12, 3.34, 3.24, 3.12–3.07, 1.38–1.32; $^{13}$C NMR (CDCl$_3$) δ 136.22, 116.00, 72.15, 64.23–64.05, 62.95–62.48, 51.40, 48.98, 16.38–15.90; $^{31}$P NMR (CDCl$_3$) δ 17.30, -2.04; Anal. Calc. for C$_{13}$H$_{29}$NO$_7$P$_2$: C, 41.82; H, 7.83; N, 3.75. Found: C, 42.14; H, 7.84; N, 3.58.

EXAMPLE 11

2-[Benzyloxyformyl(2'-propen-1'-yl)amino]-1-(diethoxyhosphiny)ethyl phosphoric acid diethyl ester A solution of allylamine (2.86 g, 0.050 mole) is cooled to 0°–5° C. by means of an ice-water bath and is treated with tetraethyl oxiranylidenebisphosphonate (Preparation 2, 3.00 g, 0.0095 mole). The mixture is stirred until the low temperature bath expires and then it is stirred overnight at room temperature. The solvent and excess allylamine are removed in vacuo and the residue is dissolved in water (70 mL). A solution of sodium hydroxide (4.75 mL, 2.0N solution in walter, 0.0095 mole) is slowly added followed by cooling the mixture to 0°–5° C. After 20 minutes, the mixture is simultaneously treated with benzylchloroformate (2.269 g, 0.0133 mole) in tetrahydrofuran (70 mL) and a solution of sodium hydroxide (2.38 mL, 4.0N solution in water, 0.0095 mole). The mixture is stirred for 45 minutes after the addition is completed. TLC (30% acetone in methylene chloride) indicates that starting material is consumed. The mixture is diluted with ether and layers are separated. The aqueous layer is extracted wilh ether (2×). The combined ether extracts are dried (magnesium sulfate), filtered and concentrated. The crude is chromatographed (flash, 300 g, 0.040–0.063 mm silica gel, 5% to 30% acetone in methylene chloride) to give 2-[benzyloxyformyl(2'-propen-1'-yl)amino]-1-(diethoxyphosphiny)ethyl phosphoric acid diethyl ester (2.716 g, 0.0054 mole, 56%) as a clear oil. $^1$H NMR (CDCl$_3$) δ 7.42–7.30, 5.87–5.70, 5.70–5.10, 5.05–5.87, 4.29–3.90, 3.72–3.65, 1.38–1.26; $^{13}$C NMR (CDCl$_3$) δ 155.91,155.42, 136.14, 132.82, 128.18, 127.81,127.74, 127.54, 117.17, 116.60, 71.72–69.18, 67.26, 67.00, 63.91, 62.87, 50.24, 50.04, 47.16, 46.10, 16.14–15.73; $^{31}$P NMR (CDCl$_3$) δ 16.43, 16.27, -1.75, -2.26; Anal. Calc. for C$_{21}$H$_{35}$NO$_7$P$_2$: C, 49.71; H, 6.95; N, 2.76. Found: C, 49.82; H, 7.03; N, 2.71.

EXAMPLE 12

1-(Diethoxyphosphinyl)-2-(diphenylmetylamino)ethyl phosphoric acid diethyl ester A solution of diphenylaminomethane (5.86 g, 0.032 mole) and tetraethyl oxiranylidenebisphosphonatc (Preparation 2, 2.026 g, 0.064 mole) in methanol (10 mL) is stirred at room temperalure for 24 hours. TLC (50% ethyl acetate in hexane) indicates some epoxide remains unreacted. Stirring is continued for another 24 hours. The solvent is removed in vacuo and the remaining residue is chromatographed (flash, 0.040–0.063 mm silica gel 50% ethyl acetate in hexane, 50% ethyl acetate in hexane plus 2% methanol) to obtain 2.063 g of the desired product slightly contaminated with 1-(diethoxyphosphinyl)ethenyl diethyl ether. This mixture (0.0944) is further chromatographed (flash, 0.040–0.063 mm silica gel, 30% acetone in hexane) to give 1-(diethoxyphosphinyl)-2-(diphenylmethylamino)ethyl phosphoric acid diethyl ester (0.728 g, 0.0016 mole, 55% overall yield) as a pale yellow oil. $^1$H NMR (CDCl$_3$) δ 7.43–7.39, 7.30–7.25, 7.21–7.16, 4.91–4.70, 4.21–3.98, 3.06, 2.25, 1.34–1.26, 1.17; $^{13}$C NMR (CDCl$_3$) δ 143.55, 143.27, 128.39, 127.23, 127.16, 126.98, 72.48, 66.39, 64.20–64.08, 62.96–62.80, 47.82, 16.35–15.16; $^{31}$P NMR (CDCl$_3$) δ 17.44,-1.90; Mass Spectrum: 500.2015 (C$_{23}$H$_{35}$NO$_7$P$_2$ requires 500.1967); Anal. Calc. for C$_{23}$H$_{35}$NO$_7$P$_2$: C, 55.31; H, 7.06; N, 2.80. Found: C, 55.08; H, 7.05; N, 2.47.

EXAMPLE 13

(1RS,1'R)-1-(Diethoxyphosphinyl)-2-[(1'-phenyl)ethylamino]ethyl diethyl ester

A solution of (R)-(+)-1-phenylethylamine (6.06 g, 0.05 mole) and tetraethyl oxiranylidenebisphosphonate (Preparation 2, 3.161 g, 0.010 mole) in methanol (20 mL) is stirred at room temperature for 72 hours. TLC (30% acetone in hexane) indicates that starting material is consumed. Solvent is removed in vacuo to obtain 2.36 g of crude material The crude is chromatographed (flash, 0.040–0.063 nm silica gel 2% methanol in a 50% acetone/hexane) three times to obtain the diastereomeric mixture (1.04 g) as a pale yellow oil. Partial separation of the diastereoisomers is achieved: less polar diastereoisomer (0.534 g, $[\alpha]_D$ +19.5°, (c=1.10, ethanol)) as a pale yellow oil and more polar diastereoisomer (0.205 g, $[\alpha]_D$ +24.5, c=0.950, elhanol) also an oil. The overall yield of the reaction is 43%.

Mixture of diastereoisomers: $^1$H NMR (CDCl$_3$) d 7.32–7.22, 4.84–4.69, 4.20–4.08, 4.38–3.78, 2.98–2.92, 1.36–1.28; $^{13}$C NMR (CDCl$_3$) δ 144.88, 144.57, 128.10, 126.65, 126.39, 126.30, 72.46, 71.94, 64.02, 62.88, 57.51, 56.79, 47.40, 47.23, 24.20, 23.87, 16.15–15.68; $^{31}$P NMR (CDCl$_3$) δ 17.72–17.42, -1.85- -2.15; Anal. Calc. for C$_{18}$H$_{33}$NO$_7$P$_2$: C, 49.43; H, 7.61; N, 3.20. Found: C, 49.60; H, 7.70; N, 3.15.

Less polar isomer: Rf 0.53 (develop plate first in 30% acetone/hexane, then in 2% methanol in 98% (50% acetone/hexne)); $^1$H NMR (CDCl$_3$) δ 7.32–7.22, 4.80–6.99, 4.21–4.05, 3.79, 2.95, 1.36–1.26; $^{13}$C NMR (CDCl$_3$) δ 145.01,128.20, 126.74, 126.41, 72.57, 64.03–63.91, 62.83–62.58, 57.62, 47.51, 23.97; $^{31}$P NMR (CDCl$_3$) δ 17.66, -2.01; Mass Spectrum: 437.1723 (C$_{18}$H$_{33}$NO$_7$P$_2$requires 437.1732).

More polar isomer: Rf 0.47 (develop plate first in 30% acetone/hexane, then in 2% methanol in 98% (acetone/hexane)); $^1$H NMR (CDCl$_3$) δ 7.32–7.22, 4.83–4.72, 4.20–4.09, 3.84. 2.95–2.90, 1.36–1.26; $^{13}$C NMR (CDCl$_3$) δ 144.81, 128.35, 126.89, 126.61, 72.19, 64.26–64.10, 62.95–62.71, 57.03, 47.46, 24.41; $^{31}$P NMR (CDCl$_3$) δ 17.55, -1.94; Mass Spectrum: 437.1732 (C$_{18}$H$_{33}$NO$_7$P)2 requires 437.1732).

EXAMPLE 14

5,5-Dimethyl-2-[2-(3-fluorobenzyl)amino-1-[(5,5-dimethyl-1,3,2-dioxaphosphorinan-2-yl)oxy]ethyl]-1,3,2-dioxaphosphorinane P,2-dioxide 3-Fluorobenzylamine (1.10 g, 0.0088 mole) in methanol (6 mL) is treated with 2,2'-(1,1-oxiranyl)bis[5,5-dimethyl-1,3,2-dioxaphosphorinane]2,2'-dioxide (Preparation 3, 1.00 g, 0.00294 mole) and allowed to stir for 16 hours. The solvents are removed in vacuo and the remaining oil is allowed to crystallize over a mixture of acetone and hexane. The crystals (monohydrated product) are collected and filtrate is concentrated to 0.951 g of crude material. The crude is chromatographed over flash silica gel (100 g, 0.040–0.063 mm) and is eluted with 4% CH$_3$OH/CH$_2$Cl$_2$ to obtain 0.515 g (0.0011 mole, 38%) of a clear thick oil which solidifies upon standing at 4°–5° C. The solid is crystallized from hexane to obtain a first crop of the title compound (0.262 g., mp 110° C.). $^1$H NMR (CDCl$_3$/TMS) δ 7.31–7.23 (m, 1H, ArH), 5.01 (m, 1H, CHO), 4.29–4.18 (m, 9H, CH$_2$OP(O), CHAr), 3.80 (d, J=13.6 Hz, 1H, CHAr), 3.22–3.16 (m, 2H, P(O)CH$_2$NH), 1.25 (s, 3H, CH$_3$), 1.22 (s, 3H, CH$_3$), 0.98 (s, 3H, CH$_3$), 0.9(s, 3H, CH$_3$); $^{13}$C NMR (CDCl$_3$) δ 162.73 (d, J=244.2 Hz, C-F), 142.23 (d, J=6.7 Hz, Ar), 129.58 (d, J=7.9 Hz, Ar), 123.43 (d, J=2.5 Hz, Ar), 114.64 (d, J=21.3 Hz, Ar), 113.6 (d, J=21.1 Hz, Ar), 78.79–76.85 (m, P(O)OCH$_2$), 70.82 (d, J=160.5, 7.5 Hz, P(O)CHOP(O)), 52.24 (CH$_2$Ph), 48.66 (CH$_2$CH), 32.32 (d, J=7.7 Hz, $\underline{C}$(CH$_3$)$_2$), 31.89 (d, $\overline{J}$=5.8 Hz, $\underline{C}$(CH$_3$)$_2$), 21.55, 21.37, 20.66, 20.04; $^{31}$P NMR (CDCl$_3$) δ 11.98 (d, J$_{PCOP}$=22.2 Hz, P(O)CHOP(O)), -6.88 (d, J$_{PCOP}$=22.2 Hz, P(O)CHOP(O)).

Anal. Calcd. for C$_{19}$H$_{30}$FNO$_7$P$_2$: C, 49.04; H, 6.50; N, 3.01; P, 13.31. Found: C, 49.22; H, 6.47; N, 3.07; P, 13.44.

EXAMPLE 15

5,5-Dimethyl-2-[2-(2-phenyl)ethylamine-1-[(5,5-dimethyl-1,3,2-dioxaphosphorinan-2-yl)oxy]ethyl]-1,3,2-dioxaphosphorinane P,2-dioxide A solution of 2,2'-(1,1 -Oxiranyl)bis[5,5-dimethyl-1,3,2-dioxaphosphorinanel]2,2'-dioxide (Preparation 3, 2.00 g, 0.0059 mole) in acetonitrile (25 ml) is treated with phenethylamine (0.784 g, 0.0065 mole) followed by potassium carbonate (0.40 g, 0.0030 mole) at room temperature and it is stirred for 16 hours. The mixture is diluted with dichloromethane and washed with brine. The aqueous layer is washed with dichloromethane (2 times). The combined organic layers are dried (magnesium sulfate), filtered and concentrated to obtain 3.023 g of crude material. The crude material is chromatographed (flash, 0.042–0.060 mm silica gel, 300 g, 1 to 3% methanol/ethyl acetate, 500 ml forerun, 228 fractions, 35 to 30 ml) to obtain 1.86 g of a slightly impure desired product. A second chromatography (flash, 0.042–0.060 mm silica gel, 138 g, 4% methanol/dichloromethane, 100 ml forerun) is necessary to obtain 1.049 g (0.0023 mole, 39%) of 5,5-dimethyl-2-[2-(2-phenyl)ethylamine-1-[(5, 5-dimethyl- 1,3,2-dioxaphosphorinan-2-yl)oxy]ethyl]-1,3,2-dioxaphosphorinane P,2-dioxide as a pale thick oil. $^1$H NMR (CDCl$_3$ ITMS) δ 7.31–7.19 (M, 5H, ArH), 5.02–4.93 (M, 1H, P(O) CHOP(O)), 4.26–4.22 (M, 2H, CH 2OP(O)), 4.15–4.09 (M, 2H, CH$_2$OP(O)), 4.03–3.79 (M, 4H, CH$_2$OP(O)), 3.24–3.19 (M, 2H, CH$_2$CHOP(O)), 3.04–2.96 (M, 1H, CHHCH$_2$Ar), 2.93–2.89 (M, 1H, CHHCH$_2$Ar), 2.84–2.80 (M, 2H, CH$_2$Ar), 1.24 (S, 3H, C$\overline{H}_3$), 1.23 (S, 3H, CH$_3$), 0.96 (S, 3H, CH$_3$), 0.87 (S,3H, CH$_3$); $^{13}$CNMR (CDCl$_3$) δ 139.87, 128.79, 128.43, 126.10, 78.09 (t, J=6.15, CH$_2$O), 71.01 (dd, J=7.5, 160.8 Hz, P(O)CHOP(O), 50.55, 49.46, 36.41, 32.55 (d, J=7.5 Hz, $\underline{C}$(CH$_3$)$_2$), 32.09 (d, J=5.6 Hz, $\underline{C}$(CH$_3$)$_2$), 21.85, 21.65, 20.90, 20.28; $^{31}$P NMR (CDCl$_3$) δ 11.87 (d, J$_{PCOP}$=22.61 Hz, $\underline{P}$(O)CHOP(O)), −7.01 (d, J$_{PCOP}$=22.40 Hz, P(O)C$\overline{H}$OP (O1). Anal. Calcd for C$_{20}$H$_{33}$O$_7$NP$_2$: C, 52.06; H, 7.2$\overline{1}$; N, 3.04. Found: C, 51.77; H, 7.33; N, 3.09

CHART A

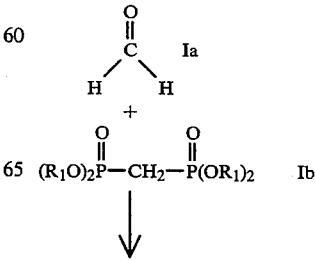

-continued
CHART A

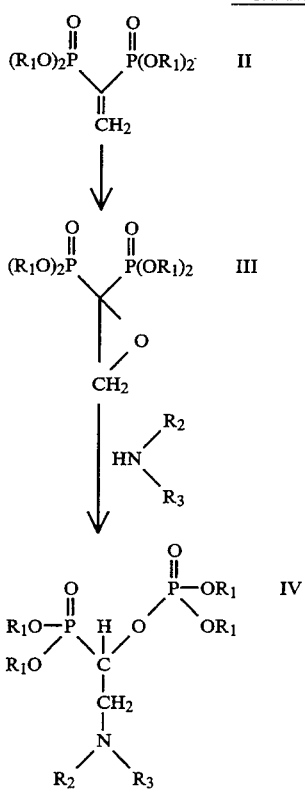

I claim:
1. A compound of formula

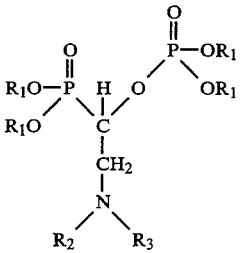 (IV)

wherein
$R_1$ is independent and selected from the group consisting of hydrogen, $C_1$–$C_{10}$ alkyl, —$C_6H_5$;
adjacent $R_1$ taken together may be —$CH_2(CH_2)_nCH_2$— or —$CH_2C(CH_3)_2CH_2$—;
$R_2$ is selected from the group consisting of hydrogen, $C_1$–$C_{10}$ alkyl, $C_3$–$C_7$ cycloalkyl, —$CH_2CH=CH_2$, —$CH_2CH_2OH$, —$CH_2(CH_2)_nAr$, —$CH_2CH_2OCH_2Ar$, —$CH(C_6H_5)_2$, and 1′- or 2′-(1′,2′,3′,4′-tetrahydro)naphthylene;
$R_3$ is selected from the group consisting of hydrogen, $C_1$–$C_{10}$ alkyl, —$CO(CH_2)_mCH_3$, —$CO_2CH_2Ar$, and —COAr;
n is 0, 1, or 2;
m is 0 thru 9;
Ar is selected from the group consisting of
(a) phenyl, 1- or 2-naphthyl, 3-indolyl, 2-, 3-, or 4-pyridinyl, or 1-imidazolyl,
(b) phenyl optionally substituted with 1 thru 5 —F or —Cl,
(c) phenyl optionally substituted with 1 thru 3 —Br, —I, —$CF_3$, —$R_4$, or —$OR_4$,
(d) phenyl substituted with —$COOR_4$, —$OCOR_4$, —$SO_2NH_2$, —$NHSO_2R_4$, and —$NHCOR_4$;
$R_4$ is $C_1$–$C_5$ alkyl;
provided, however, when $R_1$ is —$C_2H_5$, neither $R_2$ nor $R_3$ may be —$C_3H_7$;
and pharmaceutically acceptable salts thereof.
2. A compound according to claim 1 wherein
$R_1$ is independent and selected from the group consisting of $C_1$–$C_{10}$ alkyl;
$R_2$ is selected from the group consisting of $C_1$–$C_{10}$ alkyl, $C_3$–$C_7$ cycloalkyl, —$CH_2CH=CH_2$, —$CH_2CH_2OH$, —$CH_2(CH_2)_nAr$, —$CH_2CH_2OCH_2Ar$, —$CH(C_6H_5)_2$ and 1′- or 2′-(1′,2′,3′,4′-tetrahydro)naphthylene; and
$R_3$ is selected from the group consisting of hydrogen, $C_1$–$C_{10}$ alkyl, —$CO_2CH_2Ar$, and —COAr.
3. A compound according to claim 2 wherein
$R_2$ is selected from the group consisting of $C_1$–$C_{10}$ alkyl, $C_3$–$C_7$ cycloalkyl, —$CH_2CH=CH_2$, —$CH_2CH_2OH$, —$CH(C_6H_5)_2$, and 1′- or 2′-(1′, 2′, 3′, 4′-tetrahydro)naphthylene; and
$R_3$ is hydrogen.
4. A compound according to claim 3 selected from the group consisting of
2-(cyclohexylamino)-1-(diethoxyphosphinyl)ethyl phosphoric acid diethyl ester,
1-(diethoxyphosphinyl)-2-[(2′-hydroxy)ethylamino]ethyl phosphoric acid diethyl ester,
1-(diethoxyphosphinyl)-2-[2′-(1′,2′,3′,4′-tetrahydro)naphthylamino]ethyl phosphoric acid diethyl ester,
1-(diethoxyphosphinyl)-2-(2′-propen-1′-ylamino)ethyl phosphoric acid diethyl ester, and
1-(diethoxyphosphinyl)-2-(diphenylmethylamino)ethyl phosphoric acid diethyl ester.
5. A compound according to claim 2 wherein
$R_2$ is —$CH_2(CH_2)_nAr$;
$R_3$ is hydrogen;
Ar is selected from the group consisting of
(a) phenyl,
(b) phenyl substituted with 1 thru 5 —F or —Cl,
(c) phenyl substituted with 1 thru 3 —Br, —I, —$CF_3$, —$R_4$, or —$OR_4$,
(d) phenyl substituted with —$COOR_4$, —$OCOR_4$, —$SO_2NH_2$, —$NHSO_2R_4$, and —$NHCOR_4$; and
$R_4$ is $C_1$–$C_5$ alkyl.
6. A compound according to claim 5 selected from the group consisting of
2-(benzylamino)-1-(diethoxyphosphinyl)ethyl phosphoric acid diethyl ester,
2-[(3′-fluoro)benzylamino]-1-(diethoxyphosphinyl)ethyl phosphoric acid diethyl ester, and
(1RS,1′R)-1-(diethoxyphosphinyl)-2-[(1′-phenyl)ethylamino]ethyl diethyl ester.
7. A compound according to claim 6 which is 2-(benzylamino)-1-(dicthoxyphosphinyl)ethyl phosphoric acid diethyl ester.
8. A compound according to claim 6 which is 2-[(3′-fluoro)benzylamino]1-(diethoxyphosphinyl)ethyl phosphoric acid diethyl ester.
9. A compound according to claim 2 wherein
$R_2$ is —$CH_2(CH_2)_nAr$;
$R_3$ is hydrogen; and
Ar is selected from the group consisting of 1- or 2-naphthyl, 3-indolyl, 2-, 3-, or 4-pyridinyl, or 1-imidazolyl.

10. A compound according to claim 9 selected from the group consisting of
1-(diethoxyphosphinyl)-2-[(3'-pyridyl)methylamino]ethyl phosphoric acid diethyl ester,
1-(diethoxyphosphinyl)-2-[2'-(3'-indolyl)ethylamino]ethyl phosphoric acid diethyl ester, and
1-(diethoxyphosphinyl)-2-[3'-(1'-imidazolyl)propylamino]ethyl phosphoric acid diethyl ester.

11. A compound according to claim 10 which is 1-(diethoxyphosphinyl)-2-[(3'-pyridyl)methylamino]ethyl phosphoric acid diethyl ester.

12. A compound according to claim 2 wherein
$R_2$ is selected from the group consisting of $-CH_2CH=CH_2$, $-CH_2(CH_2)_nAr$, and $-CH_2CH_2OCH_2Ar$;
$R_3$ is selected from the group consisting of $-CO_2CH_2Ar$, $-CO(CH_2)_mCH_3$, and $-COAr$;
Ar is selected from the group consisting of
(a) phenyl,
(b) phenyl optionally substituted with 1 thru 5 $-F$ or $-Cl$, and
(c) phenyl optionally substituted with 1 thru 3 $-Br$, $-I$, $-CF_3$, $-R_4$, or $-OR_4$,
$R_4$ is $C_1-C_5$ alkyl.

13. A compound according to claim 12 selected from the group consisting of
2-[acetyl(3'-fluoro)benzylamino]-1-(diethoxyphosphinyl)ethyl phosphoric acid diethyl ester, and
2-[benxyloxyformyl(2'-propen-1'-yl)amino]-1-(diethoxyphosphiny)ethyl phosphoric acid diethyl ester.

14. A compound according to claim 1 wherein adjacent $R_1$ taken together are $-CH_2(CH_2)_nCH_2-$ or $-CH_2C(CH_3)_2CH_2-$.

15. A compound according to claim 14 selected from the group consisting of
5,5-dimethyl-2-[2-(3-fluorobenzyl)amino-1-[(5,5-dimethyl-1,3,2-dioxaphoshorinan-2-yl) oxy]ethyl]-1,3,2-dioxaphosphorinane P,2-dioxide, and
5,5-dimethyl-2-[2-(2-phenyl)ethylamine-1-[(5,5-dimethyl-1,3,2-dioxaphosphorinan-2-yl) oxyethyl]-1,3,2-dioxaphosphorinane P,2-dioxide.

* * * * *